(12) United States Patent
Shigeeda et al.

(10) Patent No.: US 10,160,984 B2
(45) Date of Patent: Dec. 25, 2018

(54) METHOD FOR PRODUCING PHOSPHOLIPID-CONTAINING COMPOSITION, AND PHOSPHOLIPID-CONTAINING COMPOSITION

(71) Applicant: Kaneka Corporation, Osaka-shi, Osaka (JP)

(72) Inventors: Mayumi Shigeeda, Hyogo (JP); Tatsushi Tanaka, Hyogo (JP); Inoue Yoshikazu, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 416 days.

(21) Appl. No.: 14/406,633

(22) PCT Filed: Jun. 7, 2013

(86) PCT No.: PCT/JP2013/065853
§ 371 (c)(1),
(2) Date: Dec. 9, 2014

(87) PCT Pub. No.: WO2013/187328
PCT Pub. Date: Dec. 19, 2013

(65) Prior Publication Data
US 2015/0184210 A1 Jul. 2, 2015

(30) Foreign Application Priority Data
Jun. 13, 2012 (JP) .................. 2012-134092

(51) Int. Cl.
*A61K 31/685* (2006.01)
*C12P 13/06* (2006.01)
*C12P 7/64* (2006.01)
*C11C 3/08* (2006.01)
*C07F 9/10* (2006.01)

(52) U.S. Cl.
CPC ............ *C12P 13/06* (2013.01); *A61K 31/685* (2013.01); *C07F 9/103* (2013.01); *C07F 9/106* (2013.01); *C11C 3/08* (2013.01); *C12P 7/6472* (2013.01); *C12P 7/6481* (2013.01)

(58) Field of Classification Search
CPC .................. C12N 9/16; A61K 31/685
See application file for complete search history.

(56) References Cited

U.S. PATENT DOCUMENTS

| 5,965,413 | A | 10/1999 | Sakai et al. | |
|---|---|---|---|---|
| 8,278,351 | B2 * | 10/2012 | Sampalis | A23J 7/00 514/506 |
| 2012/0100580 | A1 | 4/2012 | Tanaka et al. | |

FOREIGN PATENT DOCUMENTS

| JP | 63-233750 A | 9/1988 |
|---|---|---|
| JP | 09-121879 A | 5/1997 |
| JP | 2001-186898 A | 7/2001 |
| JP | 2004-215528 A | 8/2004 |
| JP | 2010-068799 A | 4/2010 |
| JP | 2012-249597 A | 12/2012 |
| WO | WO-2011/004794 A1 | 1/2011 |

* cited by examiner

*Primary Examiner* — Maryam Monshipouri
(74) *Attorney, Agent, or Firm* — Polsinelli PC

(57) ABSTRACT

A method for producing a phospholipid-containing composition which includes 10% by weight or more of phosphatidylserine based on the whole phospholipid-containing composition, a content of a polyunsaturated fatty acid being from 10 to 40% by weight based on the total amount of constituent fatty acids, the method including the following steps (1) and (2) in this order, and the following steps (3) and (4) in this order inexpensively and stably supplies a phospholipid-containing composition which includes phosphatidylserine to which a large amount of the polyunsaturated fatty acid is bonded at the 2-position thereof. Step (1): performing an esterification reaction of a polyunsaturated fatty acid with lysophospholipid using phospholipase A2 (PLA2) to obtain phospholipid. Step (2): adjusting an activity of PLA2 in the phospholipid to 10 U/g (phospholipid) or less after the step (1). Step (3): performing a base exchange reaction of a mixture including the phospholipid and serine in the presence of phospholipase D (PLD) to form a phospholipid-containing composition which includes phosphatidylserine. Step (4): separating the composition.

17 Claims, No Drawings

METHOD FOR PRODUCING PHOSPHOLIPID-CONTAINING COMPOSITION, AND PHOSPHOLIPID-CONTAINING COMPOSITION

RELATED APPLICATIONS

This application is a national stage application (under 35 U.S.C. § 371) of PCT/JP2013/065853, filed Jun. 7, 2013, which claims benefit of Japanese application 2012-134092, filed Jun. 13, 2012, the entire contents of which are hereby incorporated by reference.

TECHNICAL FIELD

The present invention relates to a method for producing a phospholipid-containing composition which includes phosphatidylserine, and a phospholipid-containing composition.

BACKGROUND ART

Phosphatidylserine is said to be effective in improvement of brain functions such as cognitive dysfunction, mneme, and concentration, and it is known that its effects are further improved by binding it to DHA (docosahexaenoic acid). DHA-bonded phosphatidylserine is produced by extraction from bovine brains, but recently the production has not been performed due to the influence of mad cow disease. It is also known that the DHA-bonded phosphatidylserine can be synthesized by acting DHA-bonded phosphatidylcholine or DHA-bonded phosphatidylethanolamine with phospholipase D in the presence of serine (Patent Document 1). The DHA-bonded phosphatidylcholine, which is a starting material of the DHA-bonded phosphatidylserine, is extracted from tissues of fishes including a large amount of a polyunsaturated fatty acid, such as a tuna, a bonito, a mackerel, a sardine, a saury, and a horse mackerel, or eggs obtained from chickens raised with feed including a polyunsaturated fatty acid (Patent Document 1). A method using a mixture of phosphatidylserine derived from soybean and marine DHA-bonded phosphatidylserine (a serine-glycerophospholipid conjugate) is further known (Patent Document 2). In these methods, however, a starting material is expensive and the supply is unstable.

On the other hand, as a method for producing DHA-bonded phospholipid by bonding DHA to phospholipid, there is a method in which DHA is introduced into lysophospholipid obtained by hydrolyzing a fatty acid at 2-position of phospholipid using phospholipase A2, or commercially available lysophospholipid (Patent Document 3).

According to the method described in Patent Document 3, however, a significant amount of the phospholipase A2 remains because the phospholipase A2, which is used when the fatty acid at the 2-position of the phospholipid is hydrolyzed, is not removed, or inactivation operation thereof is not performed, and thus the DHA bonded to the lysophospholipid may sometimes be separated with time during storage. When the DHA-bonded phospholipid is serylated in accordance with the method described in Patent Document 1, there is a problem in which hydrolysis occurs at the 2-position during the reaction, because the serilation of phospholipase D with serine requires water; as a result, the DHA-bonded phosphatidylserine cannot be effectively synthesized.

CITATION LIST

Patent Literatures

Patent Document 1: JP-A No. H09-121879
Patent Document 2: JP-T No. 2011-525525
Patent Document 3: JP-A No. 2010-068799

SUMMARY OF INVENTION

Technical Problem

A method for inexpensively and stably supplying phosphatidylserine having a large amount of a bonded polyunsaturated fatty acid, especially DHA-bonded phosphatidylserine, from a safe starting material is not yet known.

The object of the present invention, accordingly, is to provide a method capable of inexpensively and stably supplying a phospholipid-containing composition which includes phosphatidylserine to which a large amount of the polyunsaturated fatty acid is bonded at the 2-position thereof; and a phospholipid-containing composition which includes the phosphatidylserine having a large amount of the bonded polyunsaturated fatty acid.

Solution to Problem

In order to solve the problems described above, the present inventors have repeated a painstaking study; as a result, they have found that when a production method using phospholipid and a polyunsaturated fatty acid as starting materials and including specific steps is performed, a phospholipid-containing composition in which the polyunsaturated fatty acid is introduced in a high efficiency can be obtained, and have accomplished the present invention.

A first present invention, accordingly, relates to a method for producing a phospholipid-containing composition which includes 10% by weight or more of phosphatidylserine based on the whole phospholipid-containing composition, a content of a polyunsaturated fatty acid being from 10 to 40% by weight based on the total amount of constituent fatty acids, the method including the following steps (1) and (2) in this order, and the following steps (3) and (4) in this order:

Step (1): performing an esterification reaction of a polyunsaturated fatty acid with lysophospholipid using phospholipase A2 (PLA2) to obtain phospholipid,
Step (2): adjusting an activity of PLA2 in the phospholipid to 10 U/g (phospholipid) or less after the step (1),
Step (3): performing a base exchange reaction of a mixture including the phospholipid and serine in the presence of phospholipase D (PLD) to form a phospholipid-containing composition which includes phosphatidylserine,
Step (4): separating the phospholipid-containing composition which includes the phosphatidylserine.

In an embodiment of the present invention, at least one embodiment of an embodiment in which the PLA2 is removed from the phospholipid and an embodiment in which the PLA2 in the phospholipid is inactivated can be adopted in the step (2) described above.

In one embodiment of the present invention, after the step (1), a glycerol solution including an inorganic salt, an alcohol having 4 or less carbon atoms, and an organic solvent which is immiscible with glycerol and capable of dissolving phospholipid are added to the phospholipid; the mixture is stirred and then is allowed to stand to form an organic solvent layer including the phospholipid and a glycerol solution layer including the PLA2; and the organic solvent layer is separated from the glycerol solution layer thereby removing the PLA2 from the phospholipid in the step (2).

Here, the glycerol solution including an inorganic salt has preferably a water content of 10% by weight or less.

The organic solvent which is immiscible with glycerol and capable of dissolving phospholipid is preferably a solvent of a hydrocarbon having 5 to 8 carbon atoms and/or an ether.

The glycerol solution has preferably an inorganic salt concentration of 0.2 to 40% by weight.

The inorganic salt is preferably at least one salt selected from the group consisting of zinc sulfate, potassium chloride, magnesium chloride, magnesium sulfate, sodium chloride, and calcium chloride.

The organic solvent is preferably hexane.

The alcohol having 4 or less carbon atoms is preferably ethanol.

According to another embodiment of the present invention, after the step (1), an acid protease is added to the phospholipid to inactivate the PLA2 in the phospholipid in the step (2). Alternatively, after the phospholipid is treated with the acid protease, a neutral protease is added to the resulting phospholipid whereby the PLA2 in the phospholipid can be inactivated.

In the present invention, the polyunsaturated fatty acid is, for example, DHA. The lysophospholipid is lysolecithin derived from a plant or an egg yolk. The lysophospholipid is also lysolecithin derived from a soybean.

A second present invention relates to a phospholipid-containing composition synthesized from phospholipid derived from a plant, or phospholipid derived from a plant and an egg yolk as a starting material, which includes 10% by weight or more of phosphatidylserine, contents of DHA and linoleic acid being respectively from 10 to 40% by weight and from 15 to 40% by weight based on the total amount of constituent fatty acids Advantageous Effects of Invention According to the present invention, a phospholipid-containing composition which includes phosphatidylserine to which a polyunsaturated fatty acid is bonded at the 2-position thereof, especially DHA-bonded phosphatidylserine, can be inexpensively and stably supplied.

DESCRIPTION OF EMBODIMENTS

The present invention is explained in more detailed below. The method for producing a phospholipid-containing composition of the present invention is characterized by including specific steps. In addition, the phospholipid-containing composition of the present invention is a phospholipid-containing composition synthesized from phospholipid derived from a plant, an egg yolk, or the like, as a starting material, and is characterized by including a specific amount of the phosphatidylserine and a specific amount of the polyunsaturated fatty acid as the constituent fatty acid of the phospholipid.

The phosphatidylserine in the present invention is one kind substance of phospholipids, and exists in neurons in clumps, and serves important roles in signaling or blood flow in the brain.

The polyunsaturated fatty acid in the present invention refers to an unsaturated fatty acid having 4 or more carbon-carbon double bonds and a conjugated linoleic acid. The polyunsaturated fatty acid has functions such as improvement of a learning function, prevention of arteriosclerosis, and improvement of lipid metabolism. It is said that the polyunsaturated fatty acid has stronger antioxidation, more improved stability, and better absorbability when it is taken in a form in which the polyunsaturated fatty acid is bonded to phospholipid, compared with a form in which it is bonded to triglyceride. The polyunsaturated fatty acid may include, specifically, DHA, EPA, arachidonic acid, and the like. The DHA is preferable because it can be easily obtained and has strong functions.

The phospholipid-containing composition of the present invention includes the phosphatidylserine preferably in a content of 10% by weight or more, more preferably 10 to 80% by weight, further more preferably 30 to 80% by weight, and particularly preferably 40 to 80% by weight, based on the whole composition. When the content is less than 10% by weight, the effects of the present invention may not sometimes be obtained. The phospholipid-containing composition includes the polyunsaturated fatty acid preferably in a content of 10 to 40% by weight based on the total amount of the constituent fatty acids. When the content is less than 10% by weight, only low effects can be obtained from the polyunsaturated fatty acid, and when it is more than 40% by weight, the production may sometimes require too much cost.

<Method for Quantifying Phosphatidylserine>

The quantification of the phosphatidylserine in the phospholipid or the phospholipid-containing composition is performed by using an HPLC-ELSD apparatus in accordance with a method described in Journal of High Resolution Chromatography, 13(1990), pp 126-129. For quantifying the phosphatidylserine, a calibration curve is made using a phosphatidylserine sample, which is previously synthesized from soybean lecithin using phospholipase D in a standard method and purified in a silica gel column chromatography, and the quantification is performed based on the curve.

The method for producing a phospholipid-containing composition of the present invention basically includes the steps (1) and (2) in this order and the steps (3) and (4) in this order as described below.

<Step (1)>

An esterification reaction of lysophospholipid with a polyunsaturated fatty acid is performed using the phospholipase A2 (hereinafter which is also sometimes referred to as PLA2) to obtain phospholipid to which the polyunsaturated fatty acid is bonded. The esterification reaction may be performed according to a usual method, and it is preferable to perform the reaction in a temperature range of 30 to 80° C. and more preferably 40 to 70° C., considering an optimum temperature for an enzyme or oxidation of the fatty acids. When the temperature is lower than 30° C., enzyme activity may sometimes be low, and when it is higher than 80° C., the enzyme may sometimes be inactivated or the fatty acids may sometimes be oxidized. The reaction time is preferably from 3 to 72 hours. The amount of the PLA2 added is preferably from 1 to 100 parts by weight based on 100 parts by weight of the lysophospholipid. It is preferable that the reaction is stopped after the content of the polyunsaturated fatty acid in the constituent fatty acids is confirmed to be at least 10% by weight or more by analyzing the fatty acid composition in the phospholipid.

The phospholipase A2 used herein is an enzyme to hydrolyze a group at the 2-position of the phospholipid or to introduce a fatty acid into the 2-position of the lysophospholipid. The origin thereof is not particularly limited, but the phospholipase A2 which can be used for food is generally preferable, and it is exemplified by those derived from porcine pancreas or microorganism.

The lysophospholipid in the present invention is industrially obtained by hydrolyzing the fatty acid bonded to the 2-position of the phospholipid with the phospholipase A2. In the lysophospholipid, lysolecithin obtained from lecithin derived from a plant or an egg yolk is preferable because it is easily obtained, lysolecithin obtained from lecithin included in a soybean or an egg yolk is more preferable, and lysolecithin derived from soybean is further more preferable considering the cost. Pasty or powdery lysolecithin derived from a soybean, which is obtained by hydrolyzing the fatty acid bonded to the 2-position of the phospholipid derived from the soybean with phospholipase A2 in accordance with a usual method, includes lysophosphatidylcholine in a content of about 18 to 30% by weight, and concentrate thereof includes it in a content of 60 to 75% by weight. In addition, pasty or powdery lysolecithin derived from an egg yolk, which is obtained by hydrolyzing the fatty acid bonded to the 2-position of the phospholipid derived from the egg yolk in accordance with a usual method, includes lysophosphatidylcholine in a content of about 50 to 80% by weight.

As described above, when the lysolecithin derived from the soybean is used as the lysophospholipid, the phospholipid-containing composition finally obtained in step (2) or (4) includes a large amount of the linoleic acid as the constituent fatty acid. At that time, the content of the linoleic acid is within a range of about 15 to 40% by weight and preferably within a range of 20 to 40% by weight based on the total amount of the constituent fatty acids.

<Step (2)>

After the step (1), the activity of the PLA2 in the phospholipid, obtained in the step (1), is adjusted to 10 U/g (phospholipid) or less. This step is specifically carried out in a step (2)-1 in which the PLA2 is removed from the phospholipid or a step (2)-2 in which the PLA2 in the phospholipid is inactivated, as explained below. Both the step (2)-1 and the step (2)-2 may be carried out.

<Step (2)-1>

After the step (1), a glycerol solution including an inorganic salt, an alcohol having 4 or less carbon atoms, and an organic solvent which is immiscible with glycerol and capable of dissolving phospholipid are added to the phospholipid (an extraction solution in which phospholipid is extracted from the phospholipid-containing reaction solution obtained by the esterification reaction in the step (1) in an organic solvent, a phospholipid-containing composition obtained by distilling the organic solvent away from the extraction solution, or a phospholipid-containing composition obtained by removing the fatty acids from the above phospholipid-containing composition with acetone), and the components are mixed. The amounts of the components added may be appropriately decided considering the effect of removing PLA2. In a case where the reaction solution or the extraction solution previously includes the solvents, appropriate adjustment can be done.

After mixing, the temperature thereof is adjusted to 20 to 60° C., and the mixture is strongly stirred so that the organic solvent in which the phospholipid is dissolved is not separated from glycerol. The temperature is adjusted preferably to 40 to 60° C. After that, the mixture is thoroughly stirred and then allowed to stand, whereby a glycerol solution layer including the PLA2 and an organic solvent layer including the phospholipid are formed. Then, the organic solvent layer is separated (fractionated). The activity of the phospholipase A2 in the phospholipid is decreased by moving the PLA2, which remains in the phospholipid, to the glycerol solution layer and removing it therefrom. The addition of the predetermined solvents and fractionation, as described above, may be appropriately repeated considering improvement of a purity and an operating efficiency.

After the organic solvent layer is separated, the organic solvent is distilled away, whereby the phospholipid can be recovered. A method in which after the organic solvent is distilled away, the residue is subjected to a washing treatment with a solvent incapable of dissolving the phospholipid but capable of dissolving the fatty acid or water, and the phospholipid precipitated is recovered is preferable.

Here, the alcohol having 4 or less carbon atoms may include methanol, ethanol, propanol, and butanol, and at least one alcohol selected from the group consisting of the alcohols described above may be used. Of these, ethanol is preferable, because it has a low toxicity and thus can be utilized as a food additive.

The inorganic salt is not particularly limited so long as it has solubility in glycerol, and it is preferable to use at least one salt selected from the group consisting of magnesium chloride, magnesium sulfate, zinc sulfate, potassium chloride, sodium chloride, and calcium chloride. It is preferable to mix and use the inorganic salt in a concentration of 0.2% by weight or more based on the whole glycerol solution. When the concentration is less than 0.2% by weight, the PLA2 may sometimes be insufficiently removed. As the concentration of the inorganic salt rises, the higher the removal efficiency of the PLA2 becomes, but it is preferable that the concentration thereof is 40% by weight or less of the whole glycerol solution. When the concentration is more than 40% by weight, the viscosity of the glycerol solution increases, or the inorganic salt is precipitated, and thus the handling thereof may sometimes become difficult.

It is preferable to prepare the glycerol solution including an inorganic salt by forming an aqueous solution including the inorganic salt and then mixing it with the glycerol, considering the dispersibility of the inorganic salt in the glycerol. As the water content of the whole glycerol solution decreases, the more preferable the glycerol solution including an inorganic salt becomes, and the water content is preferably 30% by weight or less, more preferably 10% by weight or less, and further preferably 1% by weight or less. When the water content of the glycerol solution is more than 30% by weight, the PLA2 may sometimes be insufficiently removed. When the glycerol solution is prepared from the aqueous solution including the inorganic salt, it is preferable to use the glycerol solution from which water is removed.

As the organic solvent which is immiscible with glycerol and capable of dissolving phospholipid, a solvent of a hydrocarbon having 5 to 8 carbon atoms and/or an ether are/is preferable. Examples thereof may include heptane, hexane, pentane, diethyl ether, diisopropyl ether, and the like. Hexane is more preferable because it is utilized for a food use.

The solvent incapable of dissolving phospholipid but capable of dissolving a fatty acid or water may include acetone and the like.

After the step (2)-1, the lower of the phospholipase A2 activity in the phospholipid, the better, and the activity is preferably 10 U/g (phospholipid) or less and more preferably 1 U/g or less. When the activity is higher than 10 U/g, the polyunsaturated fatty acid, which has been bonded to the phospholipid in the step (1), may sometimes be detached too much.

As the step (2), the step (2)-1 may be carried out, but the following step (2)-2 may also be carried out.

<Step (2)-2>

After the step (1), an acid protease is added to the phospholipid to inactivate PLA2 in the phospholipid, thereby decreasing the activity of the phospholipase A2 in the phospholipid. The protease is an enzyme, which cleaves a peptide bond in a protein, and widely exists in animals, plants, and microorganisms.

Specifically, it is preferable that the phospholipid is extracted from the phospholipid-containing reaction solution, obtained by the esterification reaction in the step (1), with an organic solvent; the solvent is distilled away from the extracted solvent; an acid protease is added to a phospholipid-containing aqueous solution (an acidic aqueous solution), in which the phospholipid-containing composition, preferably from which the fatty acid is removed with a solvent such as acetone, is dispersed in water; and the resulting product is subjected to an enzyme reaction by stirring it for 0.5 to 48 hours while it is kept at a pre-determined temperature. When the reaction time is shorter than 0.5 hours, the effect of reducing the phospholipase A2 activity may sometimes be low, and when it is longer than 48 hours, the effect of reducing the phospholipase A2 activity may sometimes reach the limit, due to the deterioration of the phospholipid, the aggregation of the phospholipid, or the inactivation of the protease. The pre-determined temperature may be an optimum temperature for the enzyme, but a temperature lower than 60° C. is preferable in order to prevent the deterioration of the phospholipid. The acid protease may include, for example, pepsin derived from an animal, acid proteases derived from *Aspergillus niger*, and the like. The addition amount of the acid protease is preferably from 0.1 to 10 parts by weight based on 100 parts by weight of the phospholipid-containing solution.

The step (2)-2 may be finished when the treatment using the acid protease is completed, but preferably subsequently to the treatment using the acid protease, the phospholipid-containing solution is neutralized to a pH of 4.0 to 8.0, to which a neutral protease is added. More preferably, the phospholipid-containing solution is neutralized to a pH of 5.0 to 7.0, to which the neutral protease is added. It is preferable that after the neutral protease is added, the enzyme reaction is performed for 0.5 to 48 hours by stirring it while it is kept at a pre-determined temperature. When the reaction time is shorter than 0.5 hours, the effect of reducing the phospholipase A2 activity may sometimes be low, and when it is longer than 48 hours, the effect of reducing the phospholipase A2 activity may sometimes reach the limit, due to the deterioration of the phospholipid, the aggregation of the phospholipid, or the inactivation of the protease. The pre-determined temperature may be an optimum temperature for the enzyme, but a temperature lower than 60° C. is preferable in order to prevent the deterioration of the phospholipid. The neutral protease may include those derived from *Aspergillus Oryzae* or *Bacillus Subtilis*, and the like. The addition amount of the neutral protease is preferably from 0.1 to 10 parts by weight based on 100 parts by weight of the phospholipid-containing solution.

After the enzyme reaction using the acid protease, or the enzyme reaction using the acid protease and then the neutral protease is finished, a solvent capable of dissolving the phospholipid and immiscible with water (e.g., hexane, or the like) is added in an amount of 10 to 200 parts by weight based on the 100 parts by weight of the phospholipid-containing aqueous solution; the mixture is stirred; an upper layer (a solvent layer) is fractionated; and the solvent is removed from the layer, whereby the phospholipid can be extracted. When it is difficult to extract the phospholipid therefrom using the solvent described above alone, due to the increased viscosity of the phospholipid-containing aqueous solution, addition of an alcohol solvent miscible with water such as ethanol may sometimes improve an extraction efficiency. When the alcohol solvent is added, it is preferable to add it in an amount of 10 to 100 parts by weight based on 100 parts by weight of the phospholipid-containing aqueous solution. The activity of the phospholipase A2 in the phospholipid is remarkably reduced by the treatment described above.

In the above treatment, it is preferable that after the solvent is removed from the upper layer, the resulting phospholipid is washed with acetone. The washing with acetone can remove residual water, fatty acids which are separated by the hydrolysis, and the like.

After the step (2)-2, the lower of the phospholipase A2 activity in the phospholipid, the better, and the activity is preferably 10 U/g (phospholipid) or less and more preferably 1 U/g or less. When the activity is higher than 10 U/g, the polyunsaturated fatty acid, which has been bonded to the phospholipid in the step (1), may sometimes be detached too much.

<Method of Measuring Phospholipase A2 Activity>

In the present invention, a method of measuring the activity of the phospholipase A2 in the phospholipid is as described below. First, 400 mL of distilled water is added to 6 g of degreased soybean lecithin, and the mixture is stirred at room temperature for 30 minutes. To the solution including the degreased soybean lecithin is added a solution in which 0.7 g of sodium deoxycholate and 0.5 g of calcium chloride 2-hydrate are dissolved in 110 mL of water, and the mixture is homogenized at 8000 rpm for 15 minutes while it is cooled with ice. The obtained solution is used as a solution for measuring an activity. 20 mL of the solution for measuring an activity is measured and put into a 50 mL sample bottle, to which a 1 M aqueous sodium hydroxide solution is added to adjust the pH to 8.0. In 1 mL of distilled water is dispersed 20 mg of a phospholipid sample, which is to be measured, and the solution is added to the solution for measuring an activity whose pH has been adjusted to 8.0. The pH of the resulting solution is adjusted to 8.0 again, and a titer of the 20 mM sodium hydroxide solution, which is necessary for maintaining the pH at 8.0, per minute is measured. Using a calibration curve, which has been previously made with an enzyme standard solution, an activity of PLA2 in the phospholipid is calculated.

<Step (3)>

The phospholipid obtained in the step (2), or a commercially available phospholipid is mixed with serine and the base exchange reaction is performed in the presence of phospholipase D (hereinafter also referred to as "PLD"), thereby bonding the serine to the phosphate group. In this manner, the phospholipid-containing composition which includes phosphatidylserine is formed. The base exchange reaction may be performed in a two-layer method using an organic solvent capable of dissolving the phospholipid and water capable of dissolving the serine and the phospholipase D, or in a method using water alone, and any of them may be carried out. It is preferable to perform the two-layer method in terms of the solubility of phospholipid.

The method in which the reaction is performed in a two-layer system is specifically shown. First, a solution in which the phospholipid obtained in the step (2) or commercially available phospholipid is dissolved in an organic solvent is prepared. Separately, a solution in which serine and phospholipase D are dissolved in water is prepared. They are mixed and the mixture is strongly stirred to the extent that the layer separation does not occur at a temperature of, preferably, 20 to 55° C. for 0.5 to 48 hours, thereby the reaction is performed. When the reaction is performed at a temperature lower than 20° C., the reaction efficiency may sometimes be low, and when the reaction is performed at a temperature higher than 55° C., the phospholipase D may sometimes be inactivated. When the reaction time is less than 0.5 hours, the reaction efficiency may sometimes be low, and when it is more than 48 hours, side-effects such as hydrolysis may sometimes proceed.

The kind of the organic solvent used in the step (3) does not particularly matter and, for example, hexane, acetone, or ethyl acetate is used. When hexane and acetone are used at the same time, it is preferable to set a volume ratio of hexane/acetone at 20/1 to 1/1. When the volume ratio of hexane/acetone is more than 20, the reaction efficiency may sometimes be decreased because of the poor miscibility with water, and when the ratio is less than 1, the reaction efficiency may sometimes be decreased because of the decreased solubility of the phospholipid.

As for the amount of the organic solvent, there is no problem if the phospholipid can be sufficiently dissolved in that amount, and it is preferable to use an amount of 500 to 20000 parts by weight based on 100 parts by weight of the phospholipid. When the amount is less than 500 parts by weight, the solubility of the phospholipid is insufficient and the reaction efficiency may sometimes be reduced, and when it is more than 20000 parts by weight, a large amount of the solvent is used and the cost for recovery thereof or the like may be too much increased.

The amount of water is enough if the water can be mixed with a solvent and the resulting mixture can be efficiently stirred, and it is preferable to use an amount of 10 to 1000 parts by weight based on 100 parts by weight of the solvent. When the amount is less than 10 parts by weight, the reaction efficiency may sometimes be reduced because of the insufficient dissolved serine or enzyme, and when it is more than 1000 parts by weight, the reaction efficiency may sometimes be reduced because the hydrolysis by the phospholipase D becomes superior.

The amount of serine is preferably from 50 to 5000 parts by weight based on 100 parts by weight of the phospholipid, thought it depends on the amount of water used. When the amount is less than 50 parts by weight, the reaction efficiency may sometimes be reduced, and when it is more than 5000 parts by weight, the cost may sometimes be increased too much.

The phospholipase D in the present invention is an enzyme which is used for exchanging an amino group bonded to the phosphate group in the phospholipid, and may include those derived from a plant such as cabbage, those derived from pulse crops such as peanuts among the plants, and those derived from a microorganism such as *Actinomadura* or *Streptomyces*. The amount of the phospholipase D is preferably from about 20 to 1000 U per g of the phospholipid. When the amount is less than 20 U, the reaction efficiency may sometimes be reduced, and when it is more than 1000 U, the cost may be increased too much.

<Step (4)>

The phospholipid-containing composition, which includes the phosphatidylserine, formed in the step (3) is separated.

In a case where the step (3) is carried out in the two-layer system, when the reaction is finished and then the stirring is stopped, the phospholipid-containing composition, which includes the phosphatidylserine, is moved to the organic solvent layer, and thus the organic solvent layer is recovered and then the enzyme is removed therefrom by washing it with water, which is concentrated. After that, the resulting product is washed preferably with acetone and then is dried, whereby the purified phospholipid-containing composition, which includes the phosphatidylserine, can be obtained.

Alternatively, in a case where the step (3) is carried out using water alone, after the reaction is finished, for example, (1) an organic solvent such as hexane is added in an amount of 25 to 200 parts by weight based on 100 parts by weight of water to the reaction mixture, the mixture is thoroughly stirred to move the phospholipid-containing composition, which includes the phosphatidylserine, to the organic solvent layer, the resulting organic solvent layer is recovered, the layer is washed with water to remove the enzyme therefrom, and then the resulting product is concentrated; or (2) the phospholipid-containing composition, which includes the phosphatidylserine, precipitated from the aqueous layer is filtered off to recover the subject composition. After the recovery, the resulting composition is washed preferably with acetone, and is dried, whereby the purified phospholipid-containing composition, which includes the phosphatidylserine, can be obtained.

In the explanation described above, the production method of the present invention is performed by carrying out the step (1), the step (2), the step (3), and the step (4) in this order. The present invention, however, is not limited to the order as above, and according to the other aspect, the present invention can also be performed by carrying out the step (3), the step (4), the step (1), and the step (2) in this order. In such a case, after the step (4), the phospholipid obtained in the step (4) is reacted with PLA2 to hydrolyze the fatty acid bonded to the 2-position of the phospholipid, thereby obtaining the lysophospholipid. Using the resulting lysophospholipid, the step (1) is carried out. The phospholipid, obtained by reducing the PLA2 activity in the step (2) is the desired product, the phospholipid-containing composition which includes a large amount of the phosphatidylserine and the polyunsaturated fatty acid. Furthermore, as described above, in the step (3), the organic solvent layer to which the phospholipid-containing composition is moved is recovered and then it is washed with water, whereby the enzyme can be removed, and thus the production method of the present invention can be performed by carrying out the steps (3), (1), (2), and (4) in this order, if the increased cost is not considered.

In the aspect in which the step (3), the step (4), the step (1), and the step (2) are carried out in this order, in order to inhibit the proceeding of the hydrolysis reaction in the step (1), it is preferable to reduce the water content of the esterification reaction system in the step (1) within a range in which the reaction speed of the esterification reaction is not inhibited too much. For that reason, it is preferable that the esterification reaction is carried out in a reduced pressure, or the water contents of the starting materials are previously reduced in the step (1).

The method for producing a phospholipid-containing composition of the present invention can be preferably used for producing a phospholipid-containing composition for food or feed. In order to produce such a composition, only the use of the starting material which is not suitable for food and solvent such as toluene or formamide are restricted in the course of the production. The phospholipid-containing composition of the present invention can be preferably used as phospholipid for high functional food or feed. In such a case, the composition may be added to food or the composition may be taken as it is.

EXAMPLE

The present invention is more specifically explained showing Examples below, but the present invention is not limited to these Examples. In Examples, "parts" and "%" are based on the weight.

<Analysis of Composition of Fatty Acid in Phospholipid-Containing Composition>

A phospholipid-containing composition 10 mg obtained in each Example or Comparative Example was dissolved in 2 mL of isooctane, to which 1 mL of a methanol solution of 0.2 M sodium methylate was added, and the mixture was heated at 60° C. for 10 minutes while it was stirred. The resulting mixture was neutralized with acetic acid, to which water was added, and an upper layer, an isooctane layer, was recovered. The recovered layer was analyzed using a gas chromatography. In the gas chromatography, "5890 series II," manufactured by Agilent Inc., was used. As a column "DB-23," manufactured by Agilent Inc., (a length of 30 m, an inside diameter of 0.25 mm, and a film thickness of 0.25 μm) was used, and the analysis was performed at an inlet temperature of 260° C., a detection temperature of 260° C., and an oven temperature of 200° C. constant.

Example 1

A phospholipid-containing composition was obtained by carrying out steps (1) to (4) described below.

(Step (1)) Production of phospholipid with Bonded Polyunsaturated Fatty Acid

Into a 1 L glass reaction vessel was poured 200 g of glycerol (manufactured by Sakamoto Yakuhin Kogyo Co., Ltd.), to which 15 g of lysophospholipid ("SLP-WhiteLyso" manufactured by Tsuji Oil Mills Co., Ltd., lysophosphatidylcholine content standard: 18 to 30% by weight), 6 g of phospholipase A2 ("Lysonase" manufactured by Sanyo Fine Co., Ltd., Activity: 50000 U/g), DHA-containing triglyceride ("Incromega DHA-J46" manufactured by Croda Japan KK, DHA Content: 49.7% by weight), 6 g of a fatty acid hydrolyzed with an alkali in accordance with a usual manner, 6 g of glycine, 6 g of alanine, and 2 mL of a 2 M aqueous calcium chloride solution were added, and the mixture was reacted at 50° C. for 24 hours in a reduced pressure of 300 Pa while it was stirred.

(Step (2)) Recovery of Phospholipid with Reduced Phospholipase A2 Activity

After the reaction in the step (1) was finished, 100 mL of ethanol and 100 mL of hexane were added to the resulting reaction mixture to form two layers of a glycerol solution layer and an organic solvent layer. The organic solvent layer, which was an upper layer, was recovered therefrom, from which the solvent was distilled away to obtain 15 g of a phospholipid-containing recovery. To the recovery was added 50 mL of acetone, and the mixture was thoroughly stirred. The mixture was cooled at 0° C. for one hour to recover a precipitate, whereby 10 g of a phospholipid-containing composition. The activity of PLA2 remaining in the phospholipid-containing composition was 75 U/g. In the fatty acid composition in the phospholipid, the content of DHA was 16.5% by weight.

A glycerol solution was prepared by adding 10 mL of a 2 M aqueous calcium chloride solution and 10 mL of a saturated aqueous sodium chloride solution to 50 g of glycerol, and removing water therefrom at 60° C. for 30 minutes in a reduced pressure of 300 Pa. To the glycerol solution were added 10 g of the phospholipid-containing recovery obtained above, 50 mL of hexane, and 50 mL of ethanol, and the mixture was stirred at 50° C. for one hour. After the stirring was finished, the mixture was allowed to stand, and an upper layer (an organic solvent layer) was recovered. After the solvent was distilled away from the layer, to which 50 mL of acetone was added, and the mixture was allowed to stand at 0° C. for one hour, and then a precipitate of a phospholipid-containing composition was recovered therefrom. The activity of PLA2 remaining in the recovered phospholipid-containing composition is shown in Table 1.

TABLE 1

(PLA2 activity unit: U/g, content unit: % by weight)

|  | Example 1 | Example 2 | Example 3 | Example 4 | Example 5 | Example 6 | Comparative Example 1 | Comparative Example 2 |
|---|---|---|---|---|---|---|---|---|
| Activity of PLA2 remaining in phospholipid-containing composition after the step (2) | <1 | <1 | <1 | <1 | <1 | <1 | 75 | — |
| Content of phosphatidylserine in phospholipid-containing composition obtained in final step | 28 | 48 | 46 | 48 | 29 | 40 | — | 30 |
| Content of DHA or arachidonic acid in fatty acid composition in phospholipid-containing composition obtained in final step | DHA 16.2 | DHA 16.9 | DHA 34.5 | Arachidonic acid 37.7 | DHA 16.9 | DHA 14.6 | — | 0 in both cases |
| Content of linoleic acid in fatty acid composition in phospholipid-containing composition obtained in final step | 30 | 31 | 31 | 31 | 30 | 32 | — | 55 |

(Step (3)) Serylation of Recovered Phospholipid

Into a 1 L glass reaction vessel was put 8 g of the phospholipid-containing composition obtained in the step (2), with which a mixed solvent of 336 mL of hexane and 84 mL of acetone was mixed and the mixture was stirred to dissolve the composition. Then, 100 mL of a buffer solution (0.05 N sodium acetate: 0.05 N acetic acid=6:1 (a volume ratio)), 0.84 g of calcium chloride, and 60 g of L-serine were mixed therewith, and finally an aqueous solution in which 324 mg of phospholipase D (TH-2 strain: derived from *Streptomyces septatus*, Okayama Prefecture) was dissolved in 8 mL of water was added thereto. The mixture was reacted at 42° C. for 12 hours to perform serylation.

(Step (4)) Recovery and Purification of Phospholipid-Containing Composition with Phosphatidylserine The reaction solution after the step (3) was moved into a separatory funnel, which was allowed to stand to separate layers, and then a bottom layer was discarded to recover an upper layer (a solvent layer). To the recovered upper layer was added 50 mL of water, which was allowed to stand to separate layers, and then a bottom layer was discarded to recover an upper layer (a solvent layer), which procedure was repeated twice. Anhydrous sodium sulfate was added to the recovered upper layer to remove water from the solvent layer, and solid matter was removed therefrom through a filter paper. The solvent was distilled away therefrom using a rotary evaporator, and 6.4 g of a phospholipid-containing composition was recovered. The content of the phosphatidylserine in the whole composition was 28% by weight. In the constituent fatty acids in the recovered phospholipid-containing composition, the DHA content was 16.2% by weight, and the linoleic acid content was 30% by weight.

Example 2

A phospholipid-containing composition was obtained by carrying out steps (1) to (4) described below.
(Step (1)) Production of Phospholipid with Bonded Polyunsaturated Fatty Acid A reaction was performed in the same manner as in Example 1 except that "SLP-LPC70" (manufactured by Tsuji Oil Mills Co., Ltd., lysophosphatidylcholine content standard: 65 to 75% by weight) was used as the lysophospholipid.
(Step (2)) Recovery of Phospholipid with Reduced Phospholipase A2 Activity After the reaction in the step (1) was finished, 9 g of a DHA-bonded phospholipid-containing composition was obtained in the same manner as in Example 1. The activity of PLA2 remaining in the phospholipid-containing composition was 86 U/g. The DHA content in the whole constituent fatty acid composition in the phospholipid was 16.4% by weight.

A glycerol solution was prepared by adding 9 mL of a 2 M aqueous calcium chloride solution and 9 mL of a saturated aqueous sodium chloride solution to 45 g of glycerol, and removing water therefrom at 60° C. for 30 minutes in a reduced pressure of 300 Pa. To the glycerol solution were added 9 g of the phospholipid-containing recovery obtained above, 45 mL of hexane, and 45 mL of ethanol, and the mixture was stirred at 50° C. for one hour. After the stirring was finished, the mixture was allowed to stand, and an upper layer (an organic solvent layer) was recovered. After the solvent was distilled away from the layer, to which a solution in which 400 mg of citric acid was dissolved in 45 mL of acetone was added, and the mixture was allowed to stand at 0° C. for one hour, and then a precipitate of a phospholipid-containing composition was recovered therefrom. The activity of PLA2 remaining in the recovered phospholipid-containing composition is shown in Table 1.
(Step (3)) Serylation of Recovered Phospholipid Into a 1 L glass reaction vessel was put 6 g of the phospholipid-containing composition obtained in the step (2), with which a mixed solvent of 240 mL of hexane and 60 mL of acetone was mixed and the mixture was stirred to dissolve the composition. Then, 70 mL of a buffer solution (0.05 N sodium acetate: 0.05 N acetic acid=6:1 (a volume ratio)), 0.6 g of calcium chloride, and 45 g of L-serine were mixed therewith, and finally an aqueous solution in which 250 mg of phospholipase D (TH-2 strain derived from *Streptomyces septatus*, Okayama Prefecture) was dissolved in 6 mL of water was added thereto. The mixture was reacted at 42° C. for 12 hours to perform serylation.

(Step (4)) Recovery and Purification of Phospholipid-Containing Composition with Phosphatidylserine The reaction solution after the step (3) was moved into a separatory funnel, which was allowed to stand to separate layers, and then a bottom layer was discarded to recover an upper layer (a solvent layer). To the recovered upper layer was added 50 mL of water, which was allowed to stand to separate layers, and then a bottom layer was discarded to recover an upper layer (a solvent layer), which procedure was repeated twice. Anhydrous sodium sulfate was added to the recovered upper layer to remove water from the solvent layer, and solid matter was removed therefrom through a filter paper. The solvent was distilled away therefrom using a rotary evaporator, and 5 g of a phospholipid-containing composition was recovered. The content of the phosphatidylserine in the whole composition was 48% by weight. In the constituent fatty acids in the recovered phospholipid-containing composition, the DHA content was 16.9% by weight, and the linoleic acid content was 31% by weight.

Example 3

A phospholipid-containing composition was obtained by carrying out steps (1) to (4) described below.
(Step (1)) Production of Phospholipid with Bonded Polyunsaturated Fatty Acid Into a 100 mL glass reaction vessel was poured 20 g of glycerol (manufactured by Sakamoto Yakuhin Kogyo Co., Ltd.), to which 1.5 g of lysophosphatidylcholine ("SLP-LPC70" manufactured by Tsuji Oil Mills Co., Ltd.), 0.6 g of phospholipase A2 ("Lysonase" manufactured by Sanyo Fine Co., Ltd., Activity: 50000 U/g), 0.6 g of a reagent DHA (manufactured by Sigma-Aldrich, Inc., a purity of 98% or more, 0.6 g of glycine, 0.6 g of alanine, and 0.1 mL of a 2 M aqueous calcium chloride solution were added, and the mixture was reacted at 50° C. for 24 hours in a reduced pressure of 300 Pa while it was stirred.
(Step (2)) Recovery of Phospholipid with Reduced Phospholipase A2 Activity After the reaction in the step (1) was finished, 10 mL of ethanol and 10 mL of hexane were added to the resulting reaction mixture to form two layers of a glycerol solution layer and an organic solvent layer. The organic solvent layer, which was an upper layer, was recovered therefrom, and from which the solvent was distilled away to obtain 1.7 g of a phospholipid-containing recovery. The activity of PLA2 remaining in the phospholipid-containing recovery was 91 U/g. In the fatty acid composition in the phospholipid, the content of DHA was 33.2% by weight.

A glycerol solution was prepared by adding 1.2 mL of a 2 M aqueous calcium chloride solution and 1.2 mL of a saturated aqueous sodium chloride solution to 6 g of glycerol, and removing water therefrom at 60° C. for 30 minutes in a reduced pressure of 300 Pa. To the glycerol solution were added 6 mL of hexane, 6 mL of ethanol, and the phospholipid-containing recovery described above, and the mixture was stirred at 50° C. for one hour. After the stirring was finished, the mixture was allowed to stand, and an upper layer was recovered. After the solvent was distilled away from the layer, to which a solution in which 54 mg of citric acid was dissolved in 6 mL of acetone was added, the mixture was allowed to stand at 0° C. for one hour, and then a precipitate of a phospholipid-containing composition was recovered therefrom. The activity of PLA2 remaining in the recovered phospholipid-containing composition is shown in Table 1.

(Step (3)) Serylation of Recovered Phospholipid with Phospholipase D

Into a 1 L glass reaction vessel was put 1 g of the phospholipid-containing composition obtained in the step (2), with which a mixed solvent of 30 mL of hexane and 8 mL of acetone was mixed and the mixture was stirred to dissolve the composition. Then, 10 mL of a buffer solution (0.05 N sodium acetate: 0.05 N acetic acid=6:1 (a volume ratio)), 84 mg of calcium chloride, and 6 g of L-serine were mixed therewith, and an aqueous solution in which 32 mg of phospholipase D (TH-2 strain, Okayama Prefecture) was dissolved in 0.8 mL of water was added thereto. The mixture was reacted at 42° C. for 12 hours to perform serylation.

(Step (4)) Recovery and Purification of Phospholipid-Containing Composition with Phosphatidylserine The reaction solution after the step (3) was moved into a separatory funnel, which was allowed to stand to separate layers, and then a bottom layer was discarded to recover an upper layer (a solvent layer). To the recovered upper layer was added 10 mL of water, which was allowed to stand to separate layers, and then a bottom layer was discarded to recover an upper layer (a solvent layer), which procedure was repeated twice. Anhydrous sodium sulfate was added to the recovered upper layer to remove water from the solvent layer, and solid matter was removed therefrom through a filter paper. The solvent was distilled away therefrom using a rotary evaporator, and 0.8 g of a phospholipid-containing composition was recovered. The content of the phosphatidylserine in the whole composition was 46% by weight. In the constituent fatty acids in the recovered phospholipid-containing composition, the DHA content was 34.5% by weight, and the linoleic acid content was 31% by weight.

Example 4

A phospholipid-containing composition was obtained in the same manner as in the steps (1) to (4) of Example 3, except that a reagent arachidonic acid (manufactured by Sigma-Aldrich, Inc., a purity of 99% or more) was used instead of the reagent DHA in the step (1).

The activity of PLA2 remaining in the recovered phospholipid-containing recovery in the step (2) was 87 U/g. The content of the arachidonic acid in the fatty acid composition in the phospholipid was 36.4% by weight.

In the step (4), the amount of the recovered phospholipid-containing composition was 0.8 g. The content of the phosphatidylserine in the whole composition was 48% by weight. In the constituent fatty acids in the recovered phospholipid-containing composition, the arachidonic acid content was 37.7% by weight, and the linoleic acid content was 31% by weight.

Example 5

(Step (1)) Production of Phospholipid with Bonded Polyunsaturated Fatty Acid

A reaction was performed in the same manner as in the step (1) of Example 1.

(Step (2)) Recovery of Phospholipid with Reduced Phospholipase A2 Activity

After the reaction in the step (1) was finished, 100 mL of ethanol and 100 mL of hexane were added to the resulting reaction mixture to form two layers of a glycerol solution layer and an organic solvent layer. The organic solvent layer, which was an upper layer, was recovered therefrom, from which the solvent was distilled away to obtain 15 g of a phospholipid-containing recovery. To the recovery was added 50 mL of acetone, and the mixture was stirred thoroughly, which was cooled at 0° C. for one hour, and the obtained precipitate was recovered, whereby 10 g of a phospholipid-containing composition was obtained. The activity of PLA2 remaining in the phospholipid-containing composition was 75 U/g. In the fatty acid composition in the phospholipid, the DHA content was 16.5% by weight.

In 100 mL of a 0.2 M aqueous citric acid solution was dispersed 10 g of the phospholipid-containing composition, to which 1 g of acid protease ("Orientase 20A" manufactured by HBI inc) was added, and the mixture was stirred at 45° C. for 5 hours. After the stirring was finished, a 1 M aqueous sodium hydroxide solution was added to the reaction liquid to adjust a pH to 7.0, to which 1 g of neutral protease ("Peptidase R" manufactured by Amano Enzyme Inc.) was added, and the mixture was stirred at 45° C. for 3 hours. After the stirring was finished, 50 mL of ethanol and 50 mL of hexane were added to the reaction liquid, and the mixture was stirred and then allowed to stand. After that, an upper layer was recovered. The solvent in the recovered upper layer was distilled away, and 50 mL of acetone was added to the residue, which was allowed to stand at 0° C. for one hour, and precipitate of a phospholipid-containing composition was recovered. The activity of PLA2 remaining in the recovered phospholipid is shown in Table 1.

(Step (3)) Serylation of Recovered Phospholipid with Phospholipase D

In a 1 L glass reaction vessel, 7 g of the phospholipid-containing composition obtained in the step (2) was mixed with a mixed solvent of 280 mL of hexane and 70 mL of acetone, and the mixture was stirred to dissolve the composition. Then, 80 mL of a buffer solution (0.05 N sodium acetate 0.05 N acetic acid=6:1 (a volume ratio)), 0.6 g of calcium chloride, and 50 g of L-serine were mixed therewith, and an aqueous solution in which 240 mg of phospholipase D ("TH-2 strain" derived from *Streptomyces septatus*, Okayama Prefecture) was dissolved in 6 mL of water was finally added thereto. The mixture was reacted at 42° C. for 12 hours.

(Step (4)) Recovery and Purification of Phospholipid-Containing Composition with Phosphatidylserine The reaction solution after the step (3) was moved into a separatory funnel, which was allowed to stand to separate layers, and then a bottom layer was discarded to recover an upper layer (a solvent layer). To the recovered upper layer was added 40 mL of water, which was allowed to stand to separate layers, and then a bottom layer was discarded to recover an upper layer (a solvent layer), which procedure was repeated twice. Anhydrous sodium sulfate was added to the recovered upper layer to remove water from the solvent layer, and solid matter was removed therefrom through a filter paper. The solvent was distilled away therefrom using a rotary evaporator, and 6.1 g of a phospholipid-containing composition was recovered. The content of the phosphatidylserine in the whole composition was 29% by weight. In the constituent fatty acids in the composition, the DHA content was 16.9% by weight, and the linoleic acid content was 30% by weight.

Example 6

(Step (3)) Serylation of Phospholipid with Phospholipase D

Into a 1 L glass reaction vessel was put 10 g of phospholipid ("SLP-PC70" manufactured by Tsuji Oil Mills Co., Ltd.), with which a mixed solvent of 360 mL of hexane and 90 mL of acetone was mixed, and the mixture was stirred to dissolve the composition. Then, 100 mL of a buffer solution (0.05 N sodium acetate: 0.05 N acetic acid=6:1 (a volume ratio)), 1 g of calcium chloride, and 70 g of L-serine were mixed therewith, and an aqueous solution in which 350 mg of phospholipase D (TH-2 strain, Okayama Prefecture) was dissolved in 9 mL of water was finally added thereto. The mixture was reacted at 42° C. for 12 hours.

(Step (4)) Recovery and Purification of Phospholipid-Containing Composition with Phosphatidylserine The reaction solution after the step (3) was moved into a separatory funnel, which was allowed to stand to separate layers, and then a bottom layer was discarded to recover an upper layer (a solvent layer). To the recovered upper layer was added 100 mL of water, which was allowed to stand to separate layers, and then a bottom layer was discarded to recover an upper layer (a solvent layer), which procedure was repeated twice. Anhydrous sodium sulfate was added to the recovered upper layer to remove water from the solvent layer, and solid matter was removed therefrom through a filter paper. The solvent was distilled away therefrom using a rotary evaporator, and 8 g of a phospholipid-containing composition was recovered. The content of the phosphatidylserine in the whole composition was 52% by weight.

(Step (1)) Production of Phospholipid with Bonded Polyunsaturated Fatty Acid

In 50 mL of water was dispersed 9 g of the phospholipid-containing composition obtained in the step (3), whose pH was adjusted to 8.0 with a 1 M sodium hydroxide solution. To the resulting product was added 150 mg of calcium chloride 2-hydrate, and then 100 mg of phospholipase A2 ("Lysonase" manufactured by Sanyo Fine Co., Ltd., Activity: 50000 U/g) was added thereto. The resulting mixture was reacted at 50° C. for 3 hours to cleave the fatty acid at the 2-position in the phospholipid-containing composition, whereby the lysis was performed. To the reaction liquid was added 300 mL of acetone, which was cooled at 0° C. for 30 minutes, and the phospholipid-containing composition which includes the lysophosphatidylserine precipitated was obtained by recovery.

Into a 500 mL glass reaction vessel was poured 70 g of glycerol (manufactured by Sakamoto Yakuhin Kogyo Co., Ltd.), to which 5 g of the phospholipid-containing composition which includes lysophosphatidylserine, 2 g of phospholipase A2("Lysonase" manufactured by Sanyo Fine Co., Ltd. Activity: 50000 U/g), DHA-containing triglyceride ("Incromega DHA-J46" manufactured by Croda Japan KK, DHA content: 49.7% by weight), 2 g of a fatty acid, which had been hydrolyzed with an alkali in a usual manner, 2 g of glycine, 2 g of alanine, and 1 mL of a 2 M aqueous calcium chloride solution were added, and the mixture was reacted at 50° C. for 24 hours in a reduced pressure of 300 Pa while it was stirred.

(Step (2)) Recovery of Phospholipid with Reduced Phospholipase A2 Activity

After the reaction in the step (1) was finished, 35 mL of ethanol and 35 mL of hexane were added to the resulting reaction mixture to form two layers of a glycerol solution layer and an organic solvent layer. The organic solvent layer, which was an upper layer, was recovered therefrom, from which the solvent was distilled away to obtain 5.2 g of a phospholipid-containing recovery. The activity of PLA2 remaining in the phospholipid-containing composition in the recovery was 56 U/g. In the fatty acid composition in the phospholipid-containing composition, the DHA content was 14.6% by weight, and the linoleic acid content was 32% by weight. The content of the phosphatidylserine in the whole composition was 40% by weight.

A glycerol solution was prepared by adding 12 mL of a 2 M aqueous calcium chloride solution to 30 g of glycerol, and removing water therefrom at 60° C. for 30 minutes in a reduced pressure of 300 Pa. To the glycerol solution were added 30 mL of hexane, 30 mL of ethanol, and the phospholipid-containing composition described above, and the mixture was stirred at room temperature for one hour. After the stirring was finished, the mixture was allowed to stand, and an upper layer was recovered. After the solvent was distilled away from the layer, to which a solution in which 270 mg of citric acid was dissolved in 30 mL of acetone was added, and the mixture was allowed to stand at 0° C. for one hour, and then a precipitate of a phospholipid-containing composition was recovered therefrom. The activity of PLA2 remaining in the recovered phospholipid-containing composition is shown in Table 1.

Comparative Example 1

No Inactivation of PLA2

Step (1) was performed in the same manner as in that of Example 1. After the reaction in the step (1) was finished, 100 mL of ethanol and 100 mL of hexane were added thereto to form two layers of a glycerol solution layer and an organic solvent layer. The organic solvent layer, which was an upper layer, was recovered therefrom, and the solvent was distilled away therefrom to obtain 15 g of a phospholipid-containing recovery. To the recovery was added 50 mL of acetone, and the mixture was stirred thoroughly, which was cooled at 0° C. for one hour, and a precipitate was recovered, whereby 10 g of a phospholipid-containing composition was obtained. The activity of PLA2 remaining in the phospholipid-containing composition was 75 U/g. In the fatty acid composition in the composition, the DHA content was 16.5% by weight.

When the obtained phospholipid-containing composition was subjected to step (3) and step (4) in the same manner as those in Example 1 without performing step (2), phospholipid including phosphatidylserine was not detected in the recovery due to the decomposition by the remaining PLA2.

Comparative Example 2

Serylation in which Polyunsaturated Fatty Acid was not Bonded

Using a commercially available degreased soybean lecithin as a starting material, step (3) and step (4) were carried out in the same manner as in those of Example 1 without performing step (1) or step (2). As a result, the content of phosphatidylserine in the finally obtained phospholipid-containing composition was 30% by weight. DHA was not detected in the phospholipid-containing composition.

The invention claimed is:

1. A method for producing a phospholipid-containing composition which includes 10% by weight or more of phosphatidylserine based on the whole phospholipid-containing composition,
a content of a polyunsaturated fatty acid being from 10 to 40% by weight based on the total amount of constituent fatty acids in the whole phospholipid-containing composition,
the method comprising the following steps (1) and (2) in this order, and the following steps (3) and (4) in this order and wherein the method is carried out in one of the following orders (a), or (b): (a) steps (1), (2) (3) and (4); or (b) steps (3), (4) (1) and (2);

Step (1): performing an esterification reaction of a polyunsaturated fatty acid with lysophospholipid using phospholipase A 2(PLA2) to obtain phospholipid, Step (2): after Step (1), adding to the phospholipid, a glycerol solution including an inorganic salt, an alcohol having 4 or less carbon atoms, and an organic solvent which is immiscible with glycerol and capable of dissolving phospholipid thereby forming a mixture; wherein the glycerol solution including the inorganic salt has a water content of 10% by weight or less; stirring the mixture and then allowing the mixture to stand to form an organic solvent layer including the phospholipid and a glycerol solution layer including the PLA2; and then separating the organic solvent layer from the glycerol solution layer thereby removing the PLA2 from the phospholipid and thereby adjusting an activity of PLA2 in the phospholipid to 10 U/g (phospholipid) or less after the step (1), Step (3): performing a base exchange reaction of a mixture including the phospholipid and serine in the presence of phospholipase D (PLD) to form a phospholipid-containing composition which includes phosphatidylserine, Step (4): separating the phospholipid-containing composition which includes the phosphatidylserine; and wherein in the order (b), the phospholipid obtained in Step (4) is reacted with PLA 2 to hydrolyze fatty acid bonded to the 2-position of the phospholipid thereby obtaining lysophospholipid for use in Step (1).

2. The method for producing the phospholipid-containing composition according to claim 1, wherein the polyunsaturated fatty acid is docosahexaenoic acid (DHA).

3. The method for producing the phospholipid-containing composition according to claim 1, wherein the lysophospholipid is lysolecithin derived from a plant or an egg yolk.

4. The method for producing the phospholipid-containing composition according to claim 3, wherein the lysophospholipid is lysolecithin derived from a soybean.

5. The method for producing the phospholipid-containing composition according to claim 1, wherein the organic solvent which is immiscible with glycerol and capable of dissolving phospholipid is a solvent of a hydrocarbon having 5 to 8 carbon atoms and/or an ether.

6. The method for producing the phospholipid-containing composition according to claim 1, wherein the glycerol solution has the inorganic salt concentration of 0.2 to 40% by weight.

7. The method for producing the phospholipid-containing composition according to claim 1, wherein the inorganic salt is at least one salt selected from the group consisting of zinc sulfate, potassium chloride, magnesium chloride, magnesium sulfate, sodium chloride, and calcium chloride.

8. The method for producing the phospholipid-containing composition according to claim 1, wherein the organic solvent is hexane.

9. The method for producing the phospholipid-containing composition according to claim 1, wherein the alcohol having 4 or less carbon atoms is ethanol.

10. The method for producing the phospholipid-containing composition according to claim 2, wherein the lysophospholipid is lysolecithin derived from a plant or an egg yolk.

11. The method for producing the phospholipid-containing composition according to claim 10, wherein the lysophospholipid is lysolecithin derived from a soybean.

12. The method for producing the phospholipid-containing composition according to claim 2, wherein the organic solvent which is immiscible with glycerol and capable of dissolving phospholipid is a solvent of a hydrocarbon having 5 to 8 carbon atoms and/or an ether.

13. The method for producing the phospholipid-containing composition according to claim 2, wherein the glycerol solution has the inorganic salt concentration of 0.2 to 40% by weight.

14. The method for producing the phospholipid-containing composition according to claim 2, wherein the inorganic salt is at least one salt selected from the group consisting of zinc sulfate, potassium chloride, magnesium chloride, magnesium sulfate, sodium chloride, and calcium chloride.

15. The method for producing the phospholipid-containing composition according to claim 2, wherein the organic solvent is hexane.

16. The method for producing the phospholipid-containing composition according to claim 2, wherein the alcohol having 4 or less carbon atoms is ethanol.

17. The method for producing the phospholipid-containing composition according to claim 1, wherein the inorganic salt is mixed as an aqueous solution with the glycerol.

* * * * *